(12) United States Patent
Meehan et al.

(10) Patent No.: US 10,080,837 B2
(45) Date of Patent: Sep. 25, 2018

(54) STERILE PATCH PUMP

(71) Applicant: Flextronics AP, LLC, San Jose, CA (US)

(72) Inventors: Connor Meehan, Richardson, TX (US); Lopa Patel, Irving, TX (US)

(73) Assignee: FLEXTRONICS AP, LLC., San Jose, CA (US)

(*) Notice: Subject to any disclaimer, the term of this patent is extended or adjusted under 35 U.S.C. 154(b) by 0 days.

(21) Appl. No.: 15/742,398

(22) PCT Filed: Jul. 7, 2016

(86) PCT No.: PCT/US2016/041364
§ 371 (c)(1),
(2) Date: Jan. 5, 2018

(87) PCT Pub. No.: WO2017/007952
PCT Pub. Date: Jan. 12, 2017

(65) Prior Publication Data
US 2018/0193554 A1 Jul. 12, 2018

Related U.S. Application Data

(60) Provisional application No. 62/189,584, filed on Jul. 7, 2015.

(51) Int. Cl.
*A61M 5/142* (2006.01)
*A61M 5/158* (2006.01)

(52) U.S. Cl.
CPC .............. *A61M 5/14248* (2013.01); *A61M 2005/14252* (2013.01); *A61M 2005/14268* (2013.01); *A61M 2005/1585* (2013.01); *A61M 2205/123* (2013.01)

(58) Field of Classification Search
CPC .... A61M 5/14248; A61M 2005/14252; A61M 2005/1585; A61M 2005/14268; A61M 2205/123
See application file for complete search history.

(56) References Cited

U.S. PATENT DOCUMENTS

2013/0066274 A1 3/2013 O'Connor et al.
2013/0280687 A1 10/2013 Edwards et al.
2014/0296787 A1 10/2014 Agard et al.

FOREIGN PATENT DOCUMENTS

WO 2005037350 A2 4/2005
WO 2010029054 A1 3/2010
WO 2011075100 A1 6/2011

*Primary Examiner* — Bradley J Osinski
(74) *Attorney, Agent, or Firm* — Volpe and Koenig, P.C.

(57) ABSTRACT

An apparatus and method for the aseptic delivery of a biologic medication in a wearable form factor. The apparatus and method allow for standard off-the-shelf drug cartridges to be utilized without compromising the sterility of the biologic. Further, by utilizing a two part assembly, manufacturing costs are minimized.

10 Claims, 21 Drawing Sheets

STERILE PATCH PUMP

This application claims the benefit of U.S. Provisional Application No. 62/189,584 having a filing date of Jul. 7, 2015, which is incorporated by reference as if fully set forth.

FIELD OF INVENTION

The present invention is generally directed to a method and apparatus for aseptically delivering a biologic medication to a patient in a wearable form factor.

BACKGROUND

There is a strong market need for an apparatus that can enable the subcutaneous self-administration of a biologic medication in a wearable format factor. For instance, the treatment of diabetes requires the subcutaneous delivery of insulin. As a result, there are several commercially available wearable "patch pumps" that deliver a medication on the market today. These "patch pumps" incorporate the biologic medication, pumping mechanism, and infusion set into a patch that attaches to a patient's skin, thus eliminating the need external systems.

However, these commercially available "patch pumps" are prohibitively expensive to many patients due to their high manufacturing costs. In addition, the cost of these devices are further increased because they require proprietary biologic cartridges or require the biologic to be manually transferred in the patch pump. Further, insulin and other biologics must be stored at refrigerated temperatures, and therefore, there is a great amount of patient discomfort associated with wearing a cold patch pump.

Accordingly, there exists a need for an improved patch pump that overcomes these and other limitations of the commercially available "patch pumps."

BRIEF DESCRIPTION OF THE DRAWINGS

A more detailed understanding may be had from the following description, given by way of example in conjunction with the accompanying drawings wherein.

DETAILED DESCRIPTION OF THE PREFERRED EMBODIMENTS

Below are described an apparatus and methods for delivering biologics such as pharmaceutical drugs to a patient. The apparatus and methods allow for standard off-the-shelf drug cartridges to be utilized without compromising the sterility of the biologic. This enables a patient to self-administer biologics in a self-contained wearable "patch pump" form factor that is cost effective. In certain embodiments, the apparatus is adapted to enable the biologic to be stored cold while minimizing the discomfort to the patient when administered.

Figure 1:
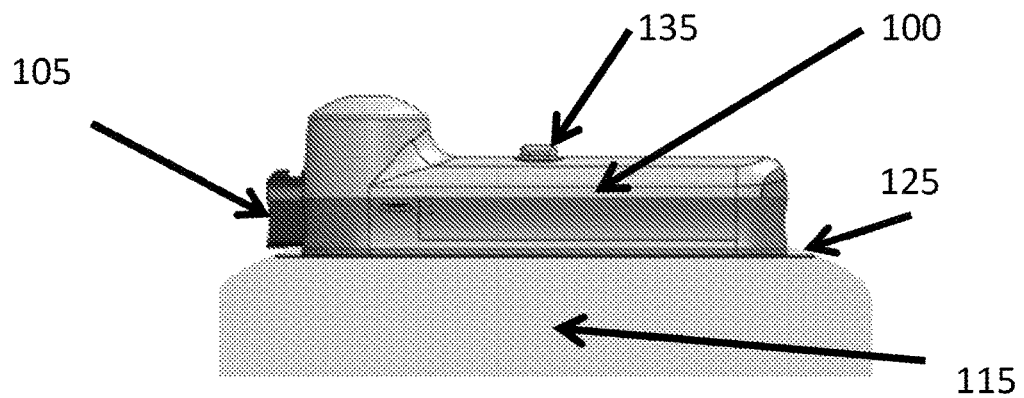
FIG. 1A is a graphic depiction of the Patch Pump on a user.
FIG. 1B is a graphic depiction of the outer casing of an embodiment of the Patch Pump.
FIG. 1C is a graphic depiction of an embodiment of the Patch Pump with the outer casing removed.
FIG. 1D is a graphic depiction of an embodiment of the Patch Pump with a sterilized and non-sterilized portion.
Figure 1:
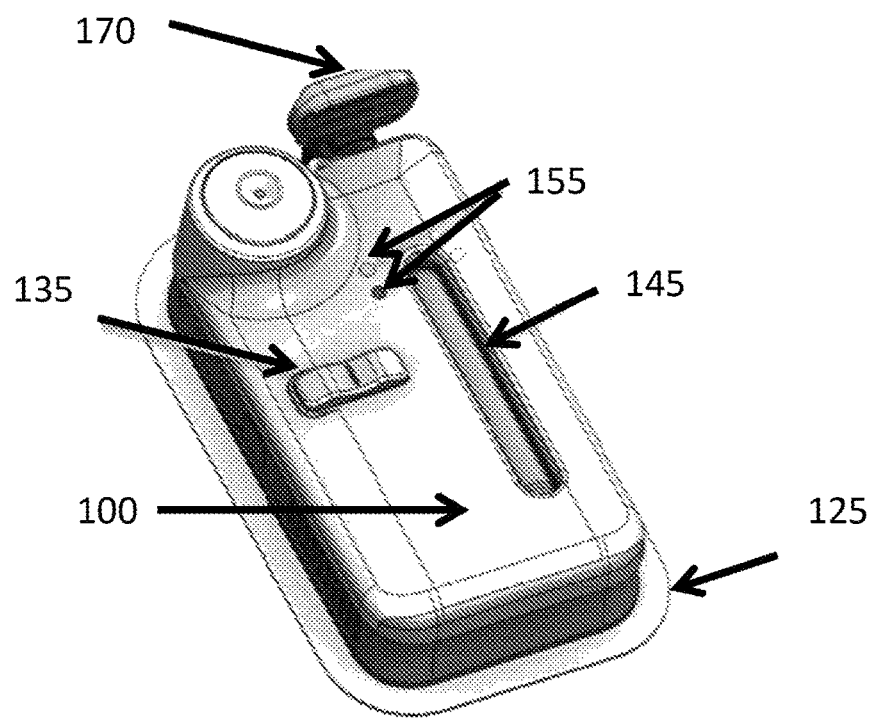
Figure 1:
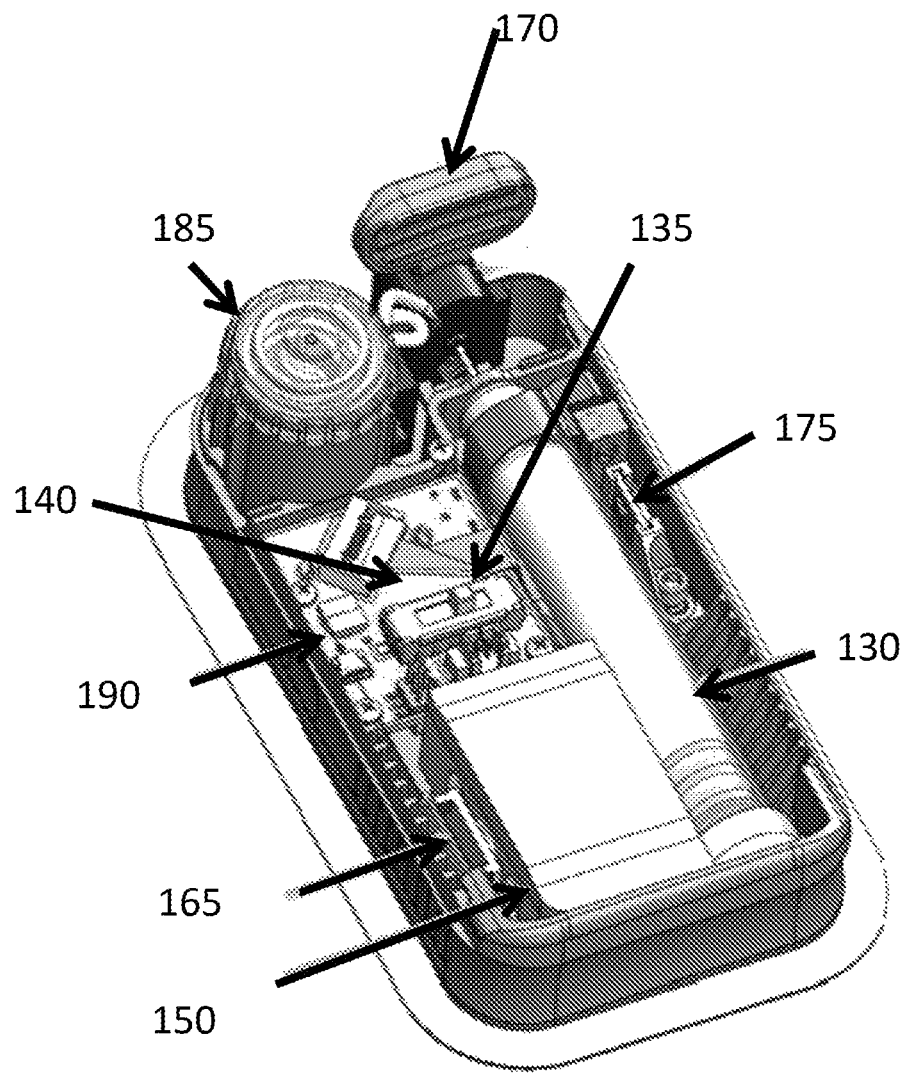
Figure 1:
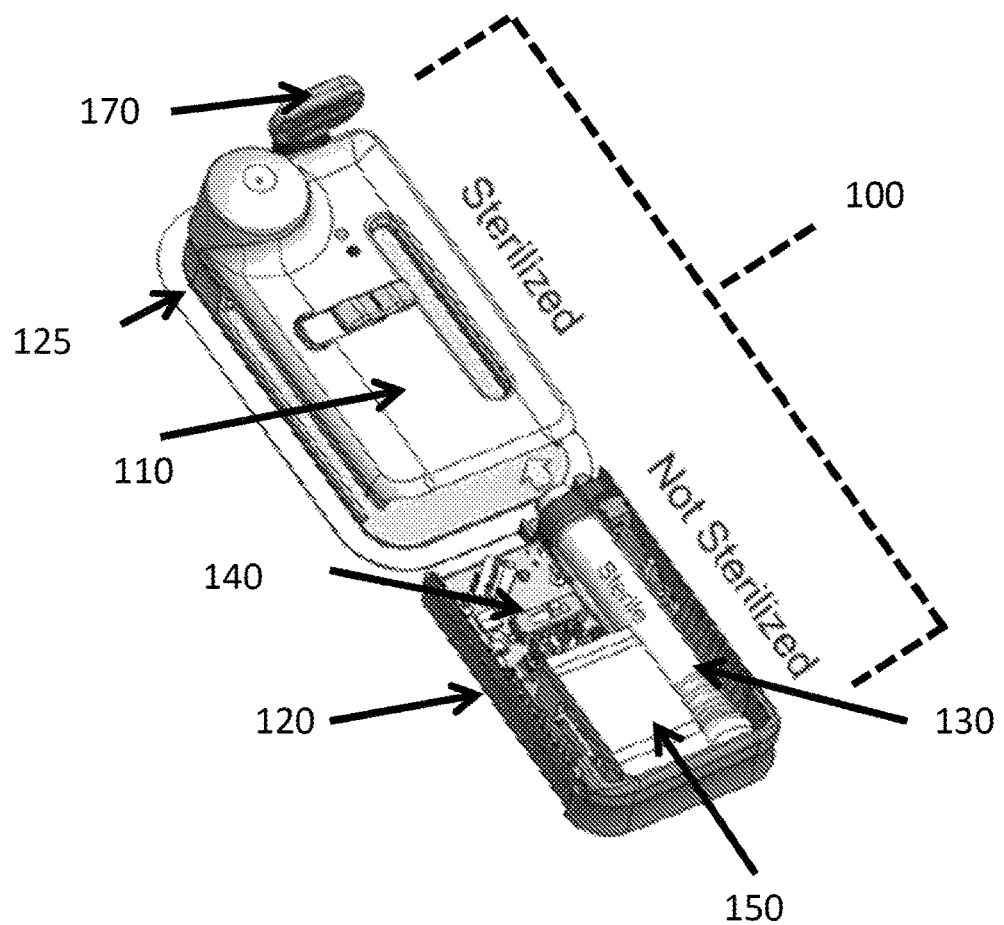

FIG. 1A is a graphic depiction of the Patch Pump 100 on a patient 115. The Patch Pump 100 includes a base 125 that contacts the patient's skin. In some embodiments, the base 125 includes an adhesive liner that affixes the Patch Pump 100 to the patient 115. The Patch Pump 100 may further include a User Flow Control Switch 135. The User Flow Control Switch 135 enables a user to pause and control the flow rate of the biologic. The Patch Pump 100 further includes a Start Button 105 that is pressed by the patient to cause the cannula 240B to be inserted into the patient and the biologic to flow from the Drug Container 130 through the cannula 240B into the patient.

As shown in FIG. 1B, the Patch Pump 100 may further include a Drug Viewing Window 145. This viewing window enables the patient to view the amount of a biologic that remains in the Drug Container 130. The Patch Pump 100 may also include one or more Visual Indicators 155. The Visual Indicators 155 provide feedback on the operational status of the system. The operational status of the system may include warnings such as an over/under temperature warning, drug expiration warning and over/under pressure warning. In addition, the operational status may include information indicating that the drug is being administered, how much time is remaining for the drug dosage to be completed and the current flow rate. The Visual Indicators may include LEDS, LCD displays or other similar display technologies known in the art. The information that is displayed by Visual Indicators may also be wirelessly transmitted to a mobile computing device such as a smart phone utilizing any of the wireless communication methods known in the art.

The Patch Pump 100 further includes a Removable Safety 170. The Removable Safety mechanically engages the Start Button 105 and prohibits the Start Button 105 from being involuntary pressed.

FIG. 1C shows additional components of the Patch Pump 100. The Patch Pump 100 also includes a Needle Insertion Mechanism 185 that is mechanically connected to the Start Button 105. In addition, the Patch Pump 100 includes an Electronic Circuit Board 140 that includes control circuitry for the Visual Indicators 155, User Flow Control Switch 135 and the Pressurization System 150. The Electronic Circuit Board 140 further includes circuitry to receive a switch input from Triggering Switch 630. In addition, the Electronic Circuit Board 140 may be communicatively connected to one or more sensors. These sensors may include Pressure Sensor 165 and Proximity Sensor 175. The Electronic Circuit Board 140 may also include a memory 190. The memory 190 may store dosing instructions for the administration of the biologic. In addition, the memory 190 may also store information regarding the administration of the biologic. This information may include, time, date, and flow rate when the biologic was administered. The Electronic Circuit Board 140 may control the Visual Indicators 155 and the Pressurization System 150 based upon the Triggering Switch 630, and the information stored in the memory and the feedback from the sensors. The Electronic Circuit Board 140 may include a communication module that enables the transmission of information stored in the memory 190 to a wireless computing device. In addition, the communication module may also receive updated dosing instructions that are subsequently stored in the memory 190.

In an embodiment shown in FIG. 1D, the Patch Pump 100 includes a Sterilized Assembly 110 and a Non-Sterilized Assembly 120. The Sterilized Assembly 110 may include the Needle Insertion Mechanism 185, the Start Button 105, the Removable Safety 170 and the Base 125. The Sterilized Assembly 110 may be sterilized by Gamma Radiation or any other similar technique known in the art. The Non-Sterilized Assembly 120 includes the Pressurization System 150, Electronic Circuit Board 140 and the Drug Container 130. The Drug Container 130 contains a biologic that was filled under aseptic conditions. Therefore, the inner part of the Drug Container 130 that contains biologic is sterilized but the outer part of the Drug Container 130 is not. This enables the Drug Container 130 to be handled under non-aseptic conditions. The Non-Sterilized Assembly 120 is configured to mechanically couple to and fit inside of the Sterilized Assembly 110.

Figure 2:
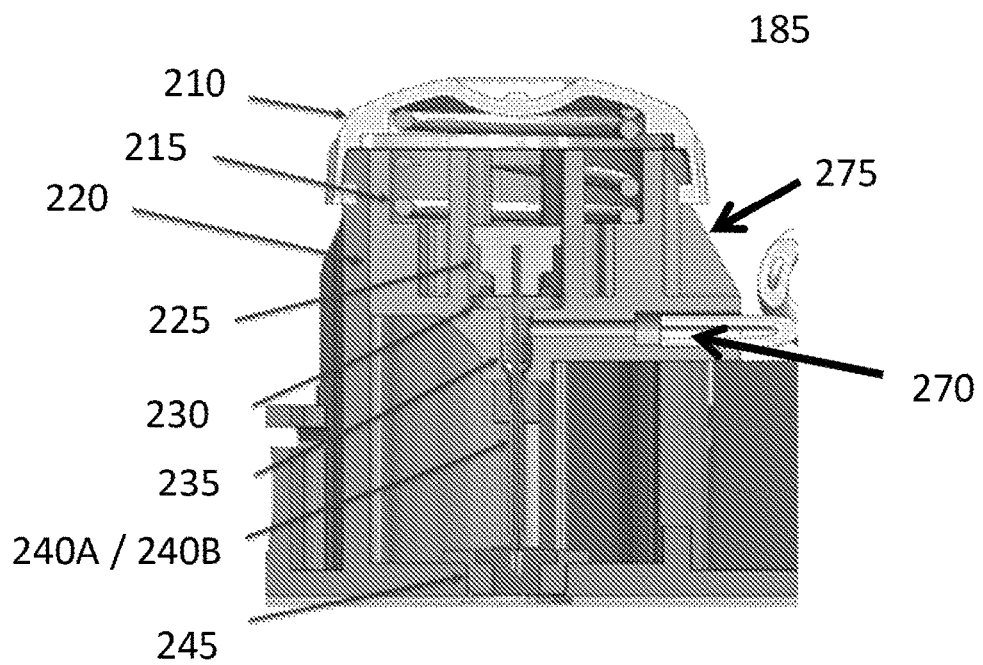
FIG. 2A is a graphic depiction of the Needle Insertion System.
FIG. 2B is a graphic depiction of a 90 degree rotation of the Needle Insertion System with the needle loaded.
FIG. 2C is a graphic depiction of the Needle Hub Assembly uncoupling the Carrier of the Needle Insertion System.
FIG. 2D is a graphic depiction of the Needle Hub Assembly.
FIG. 2E is a graphic depiction of the Needle Insertion System with the Needle retracted.
Figure 2:
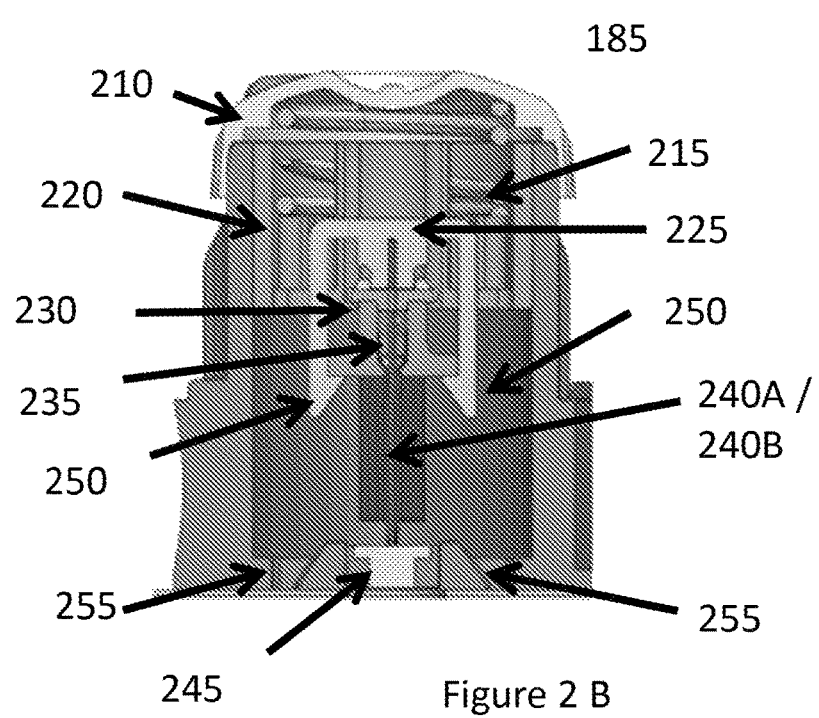

FIG. 2A is a graphic depiction of the Needle Insertion Mechanism 185. The Needle Insertion Mechanism 185 includes a Fluid Pathway 270, Cap 210 and an Exterior Septum 245. The Fluid Pathway 270 is fluidically coupled to an Internal Funnel 235 of the Needle Insertion Mechanism 185 to the biologic stored in Drug Container 130. The top of the Internal Funnel 235 includes an Internal Septum 230. A Cannula 240B extends through the Internal Septum 230 and the Internal Funnel 235 towards the Exterior 245. The Cannula 240B is mechanically connected to the Carrier 220.

The Cap 210 and the Exterior Septum 245 are separated by the height of the Needle Insertion Mechanism 185. The Cap 210 is in contact with Primary Spring 215. The Primary Spring 215 is in contact with Carrier 220. The Primary Spring 215 is compressed in direction towards the cap. When the potential energy stored in Primary Spring 215 is released, the Carrier 220 moves in a direction away from the Cap 210 and thereby causes the Cannula 240B to move towards the Exterior Septum 245. The Carrier 220 further includes a Carrier Arm 275. The movement of the Carrier Arm 275 triggers the release of the potential energy stored in the Primary Spring 215.

Figure 2C:
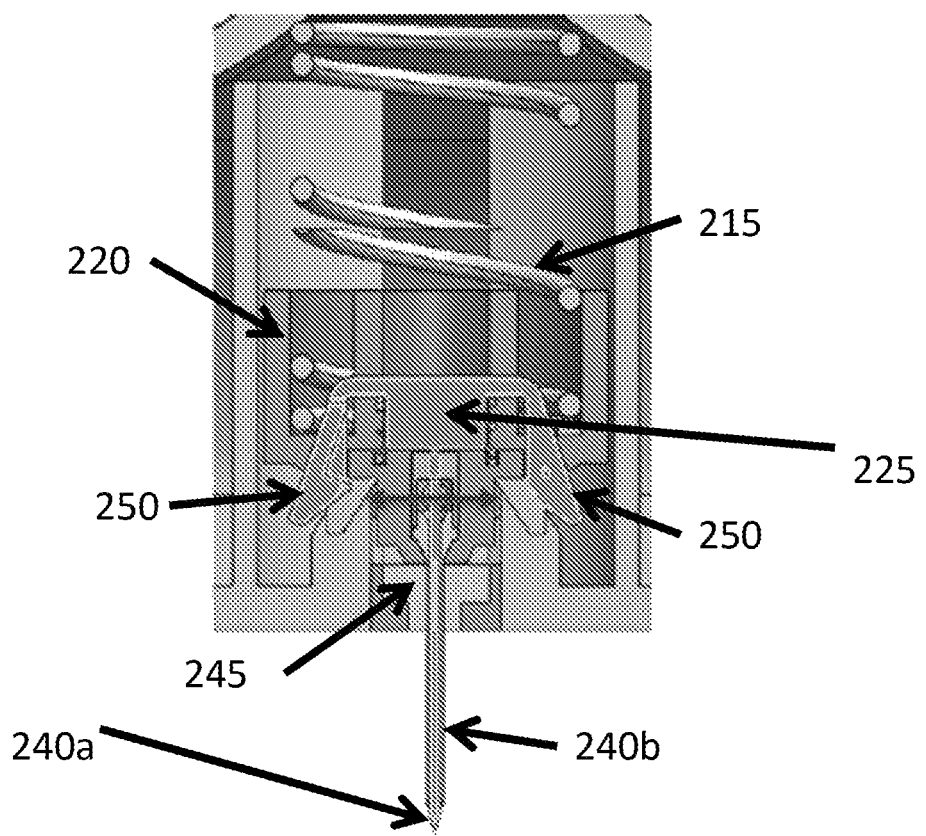

The Needle Insertion Mechanism 185 further includes a Needle Hub Assembly 225. The Needle Hub Assembly 225 is mechanically coupled to the Carrier 220 by Release Tabs 250. As shown in FIG. 2B, the mechanical coupling by the Release Tab enables the Needle Hub Assembly to move with the Carrier 220 when the potential energy stored in the Primary Spring 215 is released. The Release Tabs 250 have an inclined shape that engages Tab Separators 255 as the Needle Hub Assembly 225 moves away from the Cap 210. As shown in FIG. 2C, the engagement of the Release Tabs 250 with Separators 255 causes the Needle Hub Assembly 225 to uncouple from Carrier 220.

Figure 2D:
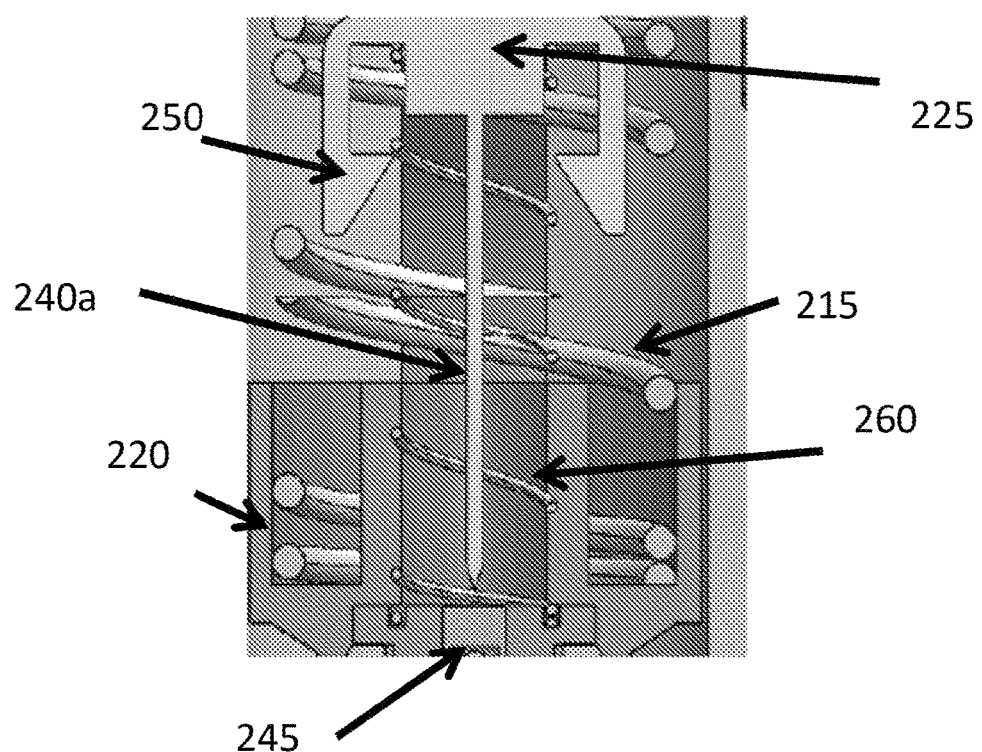

As shown in FIG. 2D, the Needle Hub Assembly 225 further includes a Needle 240A. The Needle Hub Assembly 225 is coupled to the Carrier 220 so that Needle 240A is coaxially inside of Cannula 240B. In addition, the Needle Hub Assembly further includes a Secondary Spring 260 is coaxially located around the Cannula 240B. When the Release Tabs 250 uncouple from the Carrier 220, the potential energy stored in Secondary Spring 260 is released. The release of the potential energy causes the Needle Hub Assembly 225 to retract towards Cap 210. The retraction of the Needle Hub Assembly causes the Needle 240A to be drawn out of the Cannula 240B thereby creating an unobstructed fluid path from the Cannula 240B to the Fluid Pathway 270.

Figure 2E:
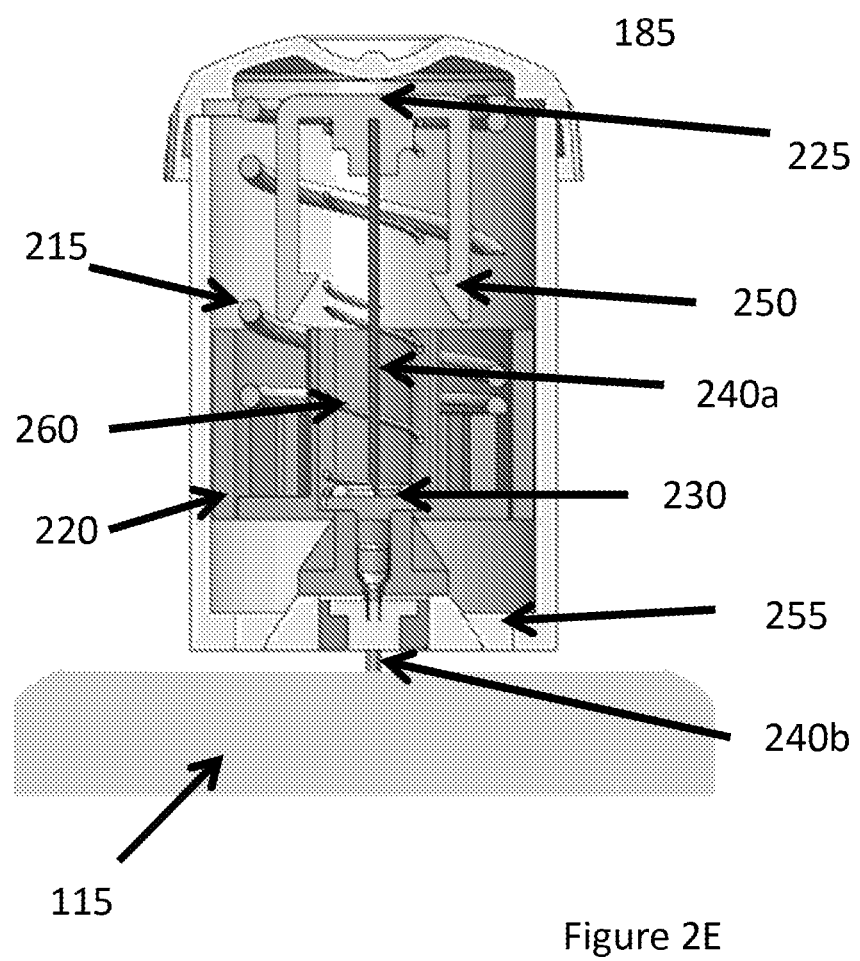

FIG. 2E shows the Needle Hub Assembly 225 fully retracted and the Cannula 240B inserted in the patient 115. As a result of the insertion, a fluid pathway is created from the Drug Container 130 to the Patient 115.

Figure 3A:
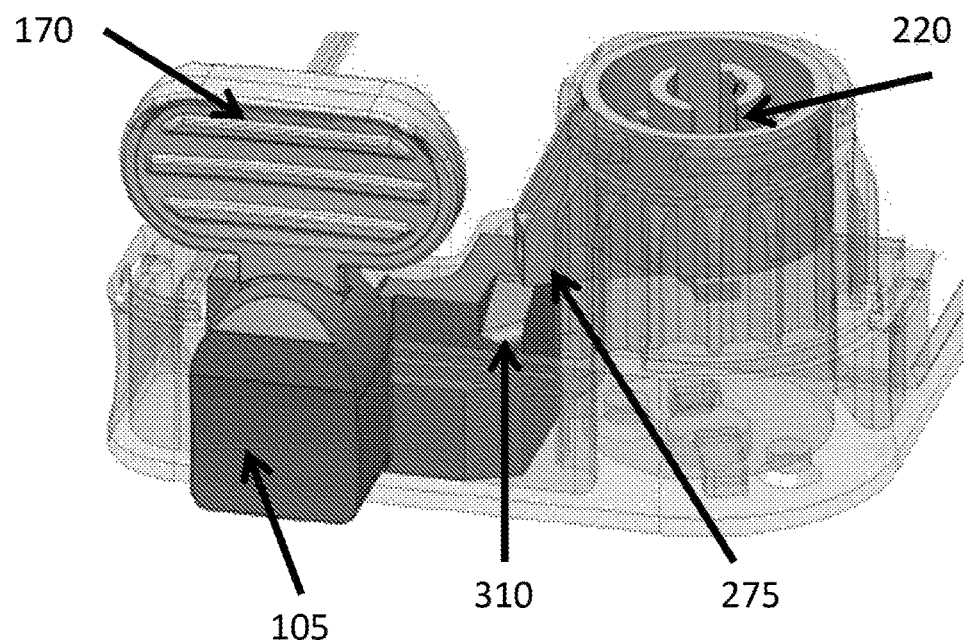
FIG. 3A is an end view of the Patch Pump.

FIG. 3A shows an end view of the Patch Pump 100. The end view shows the mechanical engagement of the Removable Safety 170 and the Start Button 105. In addition, the end view shows the Carrier Arm 275 is in physical contact with a flat portion 325 of the Start Button 105. The physical contact restrains the Carrier 220 from moving away from Cap 210 due to the spring force exerted by the Primary Spring 215. The friction between the Carrier Arm 275 and the flat surface 325 provides a sufficient force to avoid the accidental discharge of the potential energy stored in the Primary Spring 215. The Start Button 105 further includes a declined ramp.

Figure 3B:
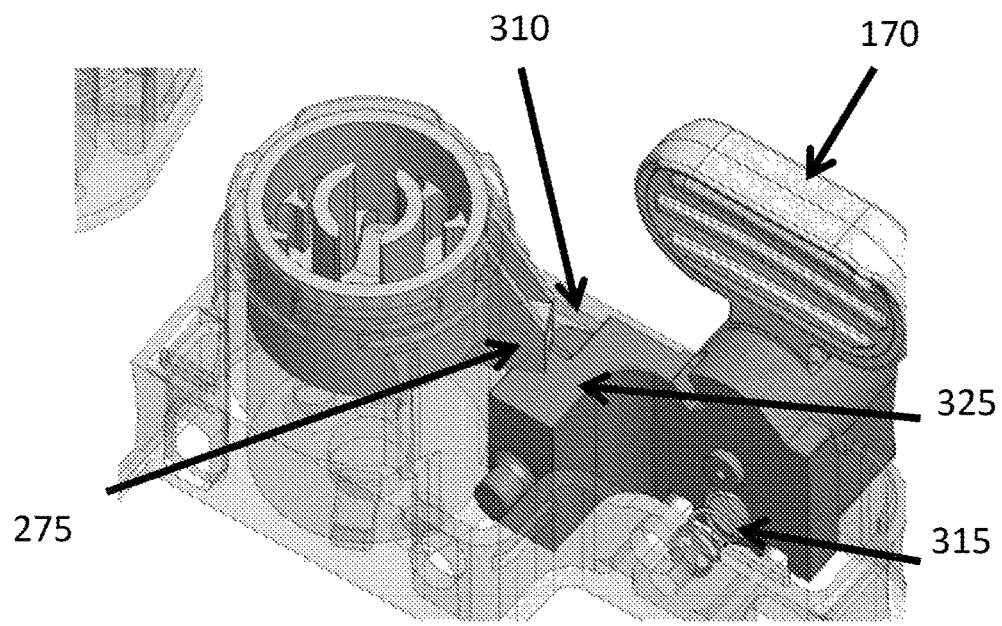
FIG. 3B is a rotated view of FIG. 3A.

FIG. 3B is a rotated view of FIG. 3A. FIG. 3B further shows Start Button Spring 215. Start Button Spring 215 aids in preventing the accidental release of the energy stored in the Primary Spring 215 by forcing the Start Button 105 away from the move away from the Carrier Arm 275 when armed. Once the Cannula 240B is inserted into the patient, the Start Spring 315 provides a force to lock the push button against the Carrier Arm 275.

Figure 3C:
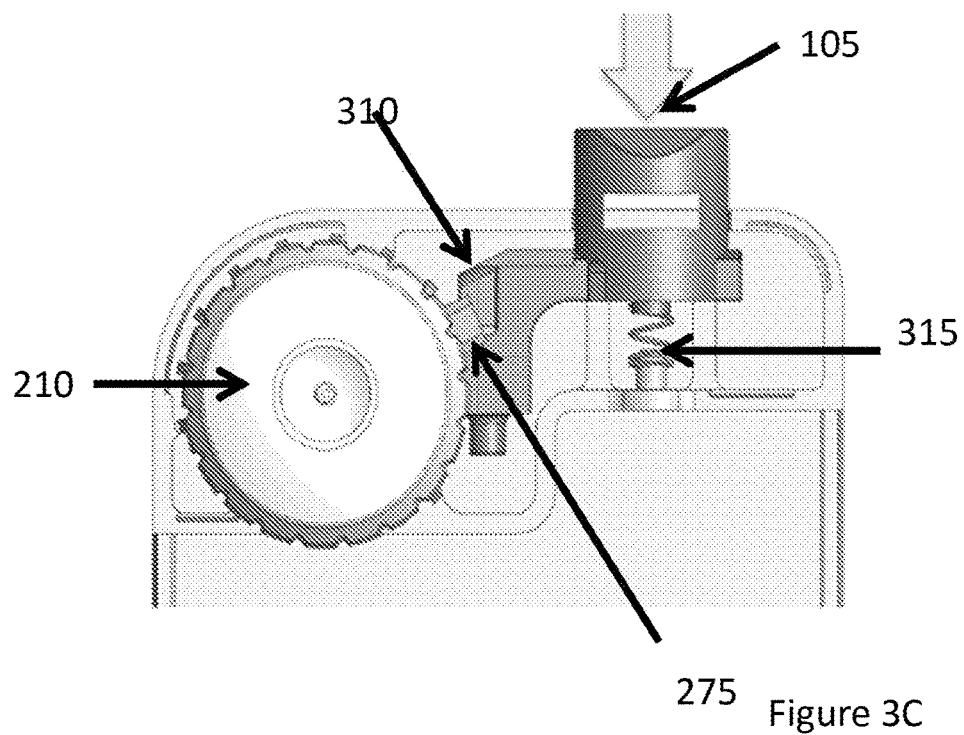
FIG. 3C is a top view of FIG. 3A.

FIG. 3C is a top view of FIG. 3A and further shows the engagement of the Carrier Arm 275 and the Declined Ramp 310.

Figure 3D:
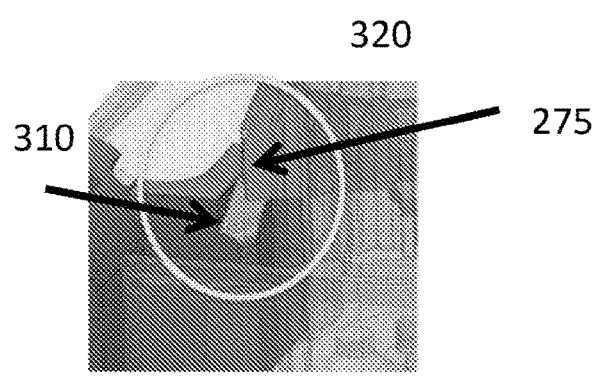
FIG. 3D is a zoomed in view of the declined ramp.

FIG. 3D is a zoomed in view of the Carrier Ramp 275 sliding down the Declined Ramp 310.

Figure 3E:
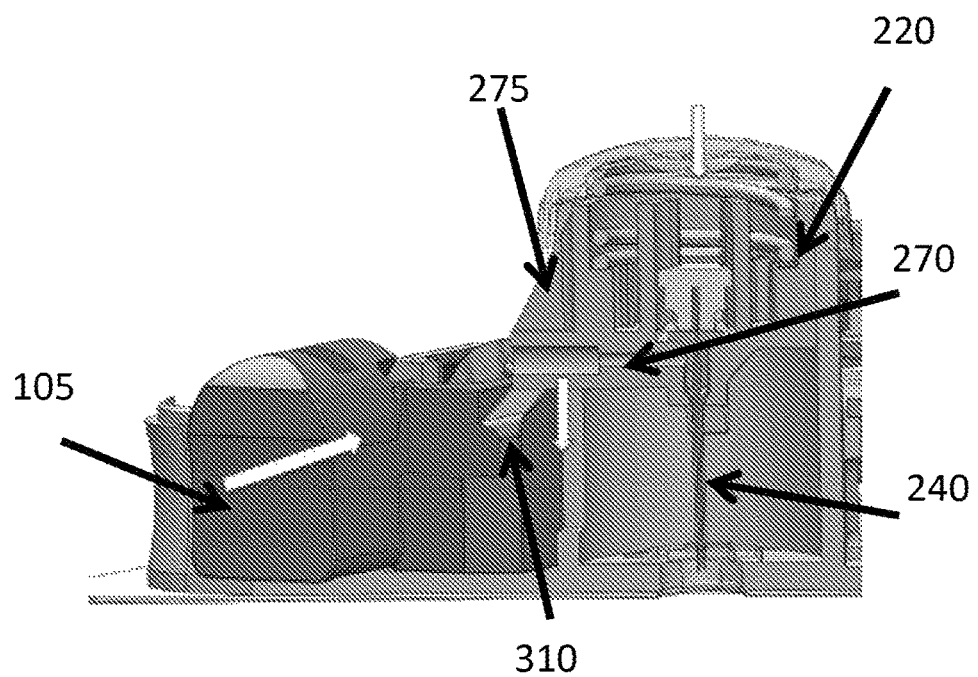
FIG. 3E is an end view of the Patch Pump with the needle loaded.
Figure 3F:
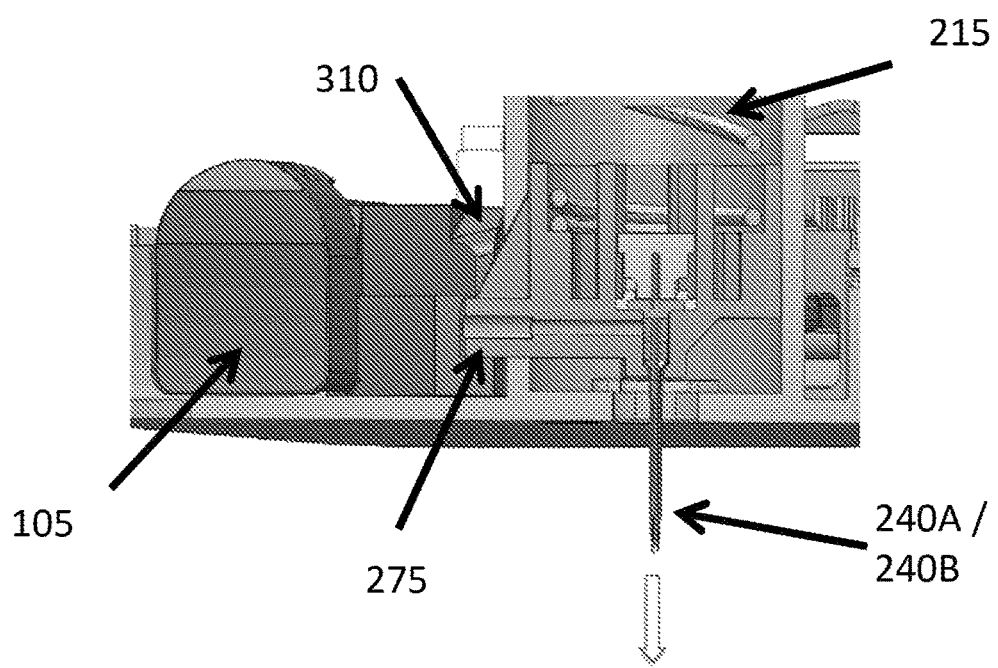
FIG. 3F is an end view of the Patch Pump with the needle inserted.
Figure 3G:
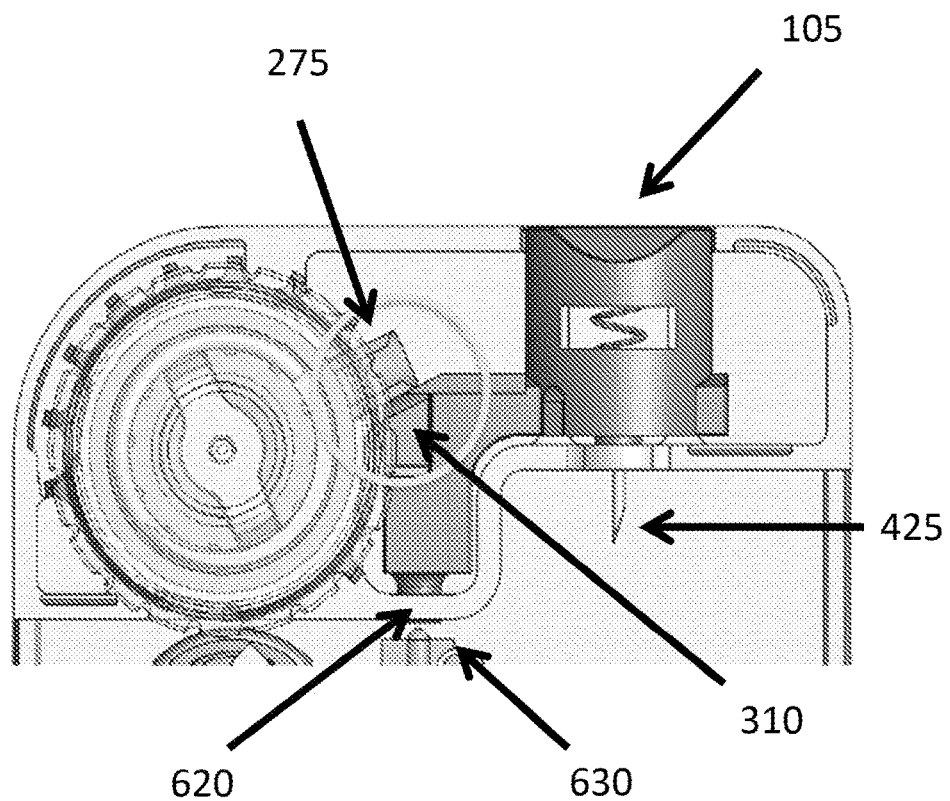
FIG. 3G is a top view of the Patch Pump with the needle inserted.

FIG. 3E and FIG. 3F show the movement of Carrier 220 results from Start Button 105 being pushed. The movement of the Start Button 105 causes Carrier Arm 275 to engage Declined Ramp 310. As the Declined Ramp 310 passes under the Carrier Arm 275, the potential energy stored in Primary Spring 215 is released causing the Carrier 220 to move away from Cap 210 thereby inserting Cannula 240B into the patient. Once the Declined Ramp 310 completely passes under the Carrier Arm 275, the Carrier Arm 275 moves behind the Push Button 105, thereby locking the Start Button 105 and the Carrier 220 in place. This orientation is further depicted by FIG. 3G. The locking of the Start Button 105 inhibits the Start Button 105 from being subsequently pressed. The locking of the Carrier 220 provides an additional force to stop the carrier from moving away when the Cannula 240B is inserted into the patient.

Figure 4A:
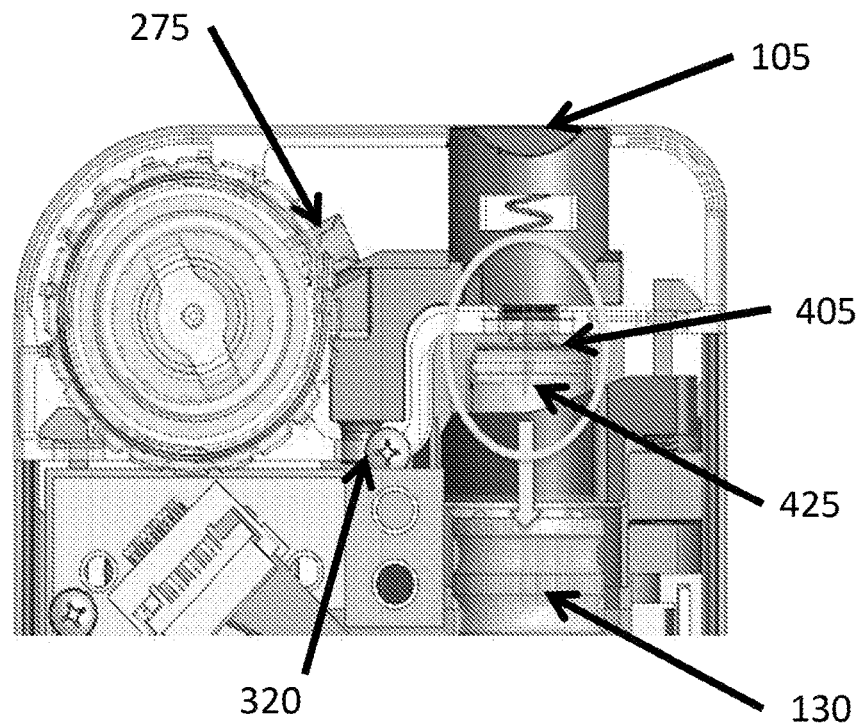
FIG. 4A is a top view of the Patch Pump with the needle inserted.
Figure 4B:
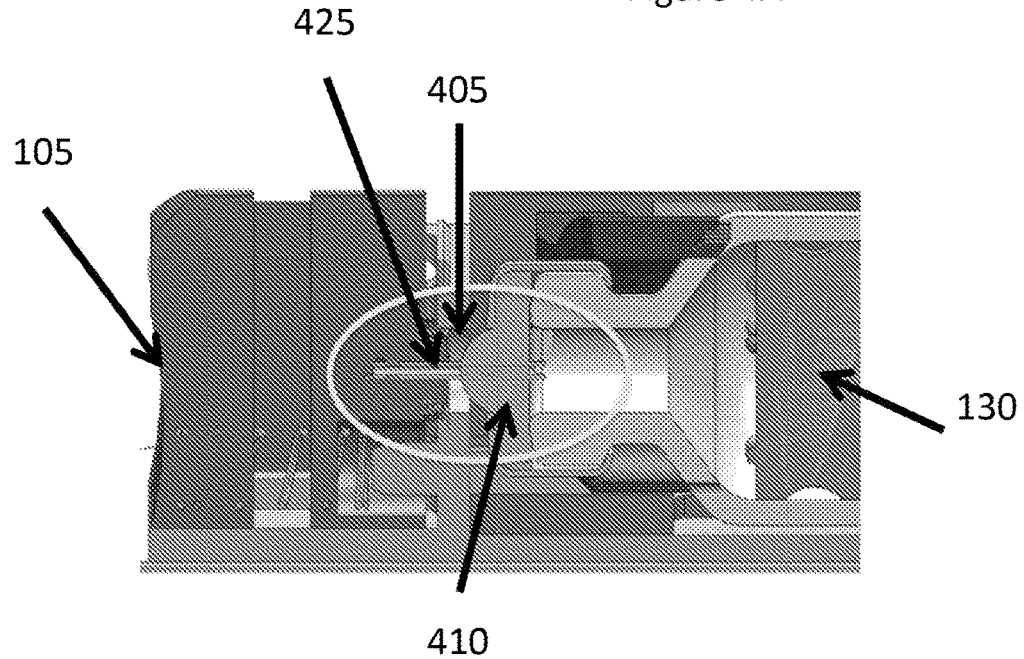
FIG. 4B is a zoomed in view of the Fluid Patch needle puncturing the Sterile Drug Barrier.

The creation of the fluid path from the Drug Container 130 to the Fluid Pathway 270 is shown in FIG. 4A. When the Start Button 105 is fully pressed, the Fluid Path Needle 425 pierces the Sterile Drug Barrier 405 and the Drug Container Septum 410. The Fluid Path needle 425 is hollow and fluidically coupled to the Fluid Pathway 270, thereby enabling the flow of biologics stored in the Drug Container 130 to Cannula 240B. A zoomed in view of the Fluid path Needle 425 piercing the Sterile Drug Barrier 405 and the Drug Container Septum 410 is shown in FIG. 4B.

Figure 5A:
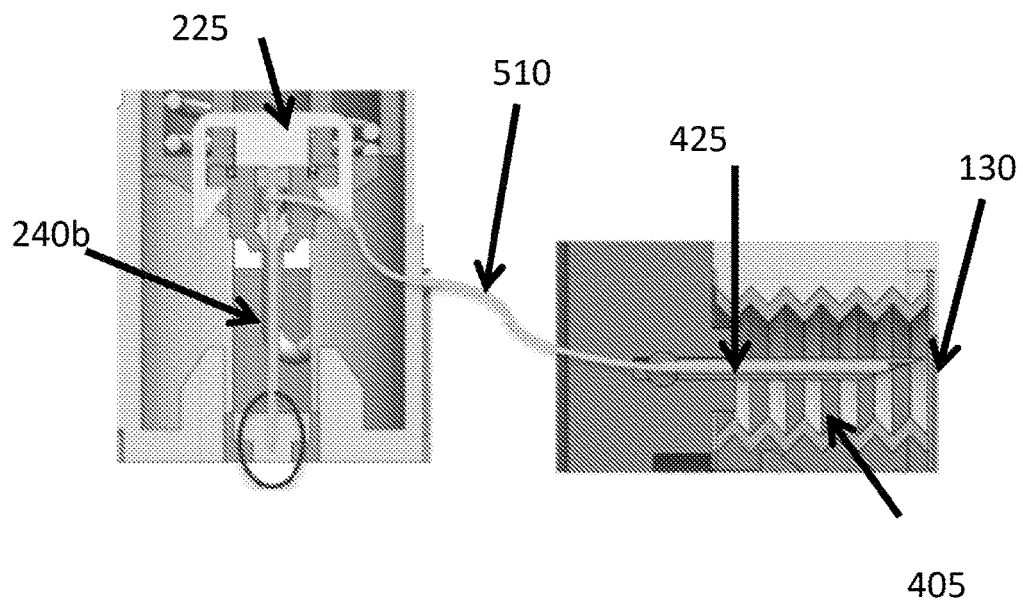
FIG. 5A is a graphic depiction of the fluid pathways of the Patch Pump.
Figure 5B:
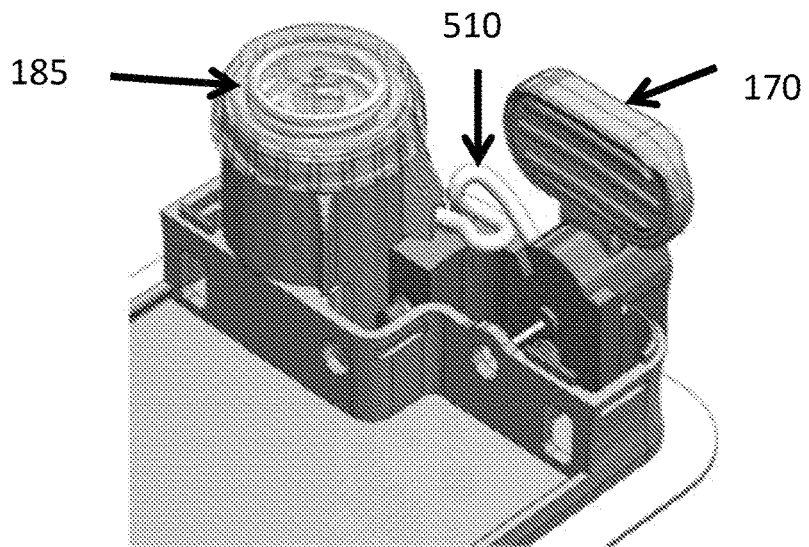
FIG. 5B is an end view of the fluid pathways of the Patch Pump.
Figure 6:
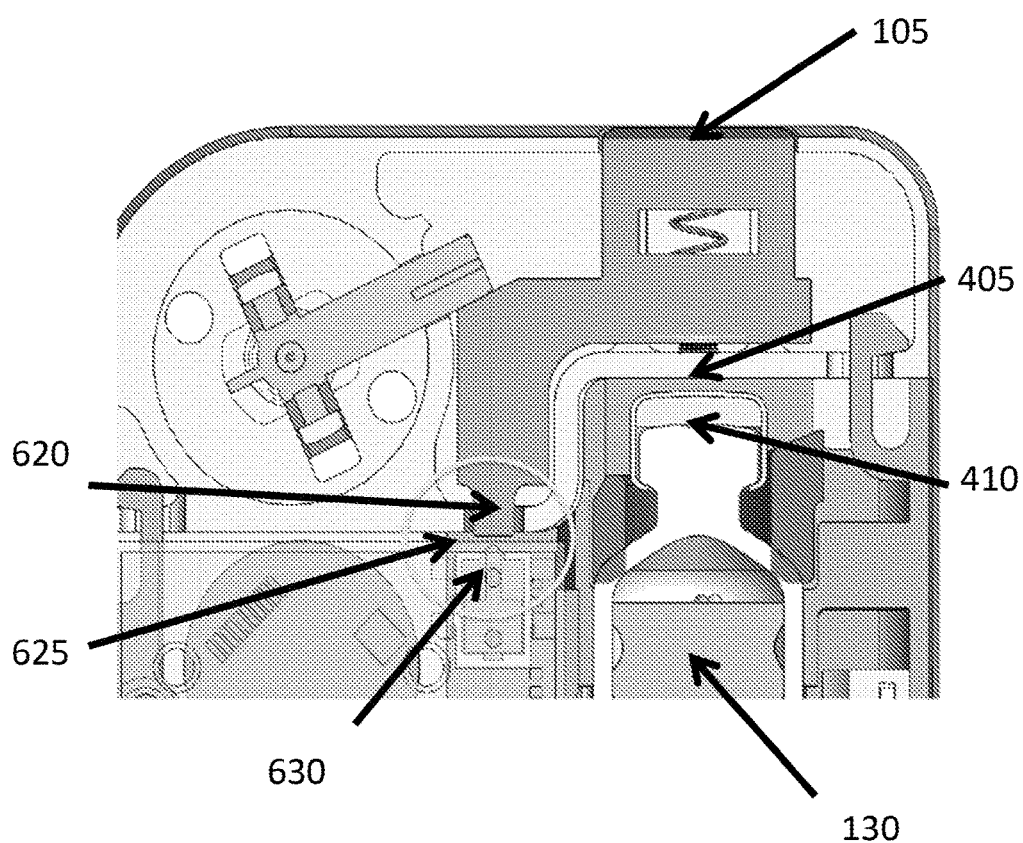
FIG. 6 is a top view of the Patch Pump.

FIGS. 5A and 5B depict the fluidic coupling of the Drug Container 130, through Fluid Path Needle 425 and Tubing 510 to Cannula 240B.

The pressing of the Start Button 105 causes Triggering Post 620 to activate Triggering Switch 630 through Sterile Switching Barrier 625. The Sterile Switching Barrier 625 may be in the form of a flexible barrier and may in an accordion-like shape.

Figure 7:
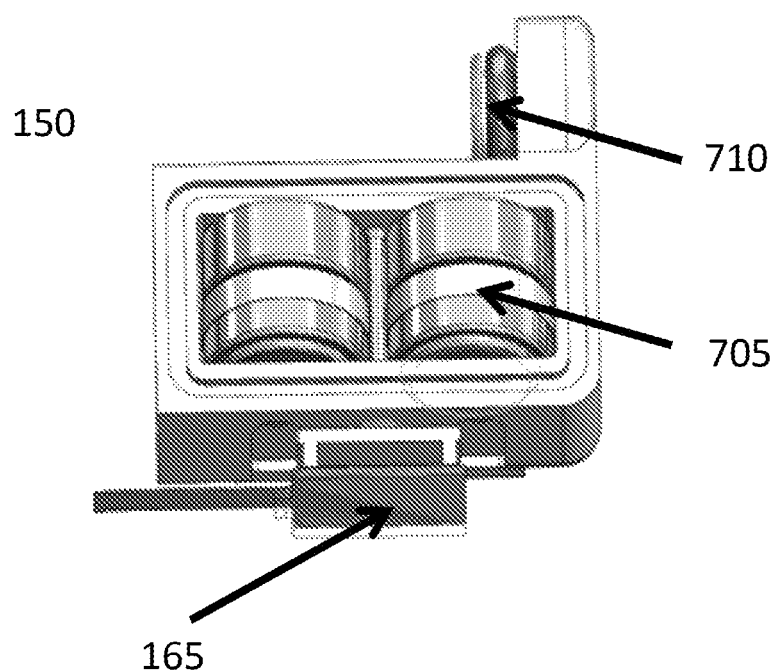
FIG. 7 is a depiction of an embodiment of the fluid drive system.
Figure 8:
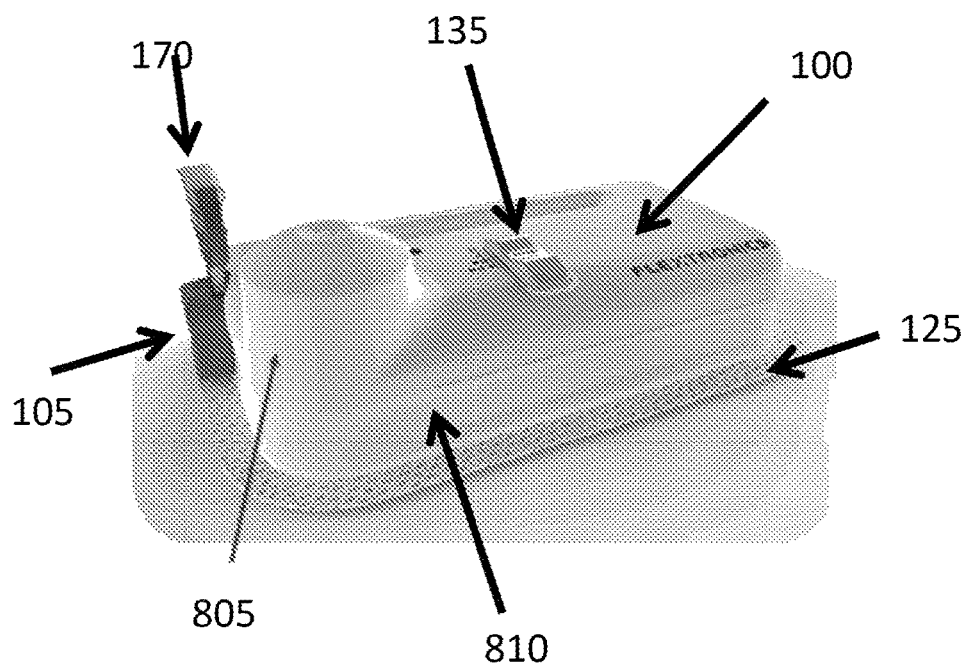
FIG. 8 is a side view of the Patch Pump.

The Pressurization System 150 is graphically depicted in FIG. 7. The Pressurization System 150 may include one or more hydrogen generators 705. Alternatively, other pressurizing means such as pumps may also be used. The one or more hydrogen generators produce a pressuring gas in response to control signal from the Electronic Circuit Board 140. The pressurizing gas flows through coupling 710 into the Drug Container 130. The pressurizing gas forces the biologic to flow through the Fluid Path Needle 425 and ultimately into the patient 115.

In an embodiment, the Patch Pump 100 includes a top outer cover 805 and bottom outer cover 810 that are mechanically coupled. The bottom outer cover 810 thermally isolates the Drug Container 130 from the Patient 115. This thermal isolation can be accomplished through the utilization of materials with low thermal conductivity such as porous structural foam plastics, glass impregnated plastics or over molded ethylene propylene diene monomer (M-class) (EPDM) foam rubber. In addition, the bottom outer cover may include an additional outer thin shell that insulates a cold Patch Pump 100 from a patient's skin. In another alternative embodiment, the Base 125 may be made of one of the materials with low thermal conductivity.

Figure 9:
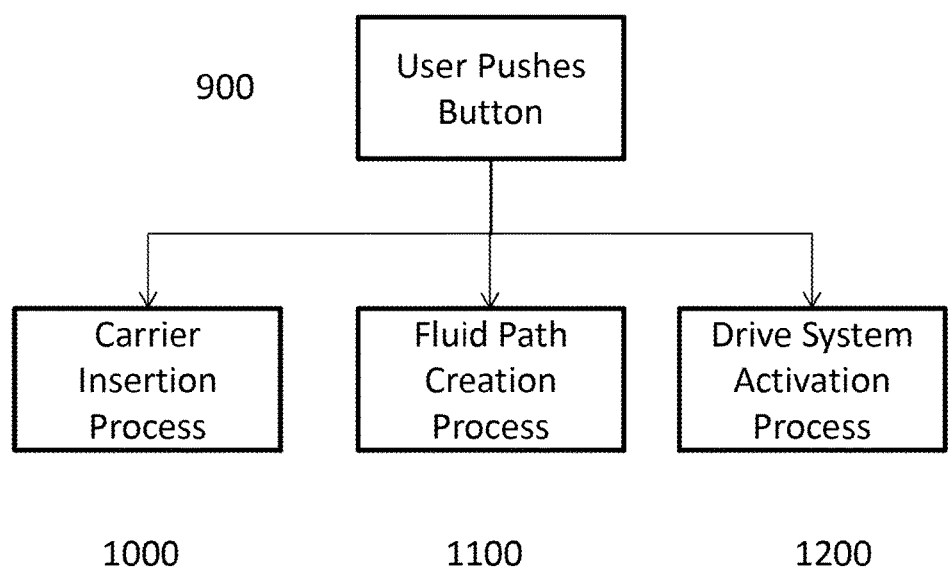
FIG. 9 is a flow diagram of the operation of the patch pump.
Figure 10:
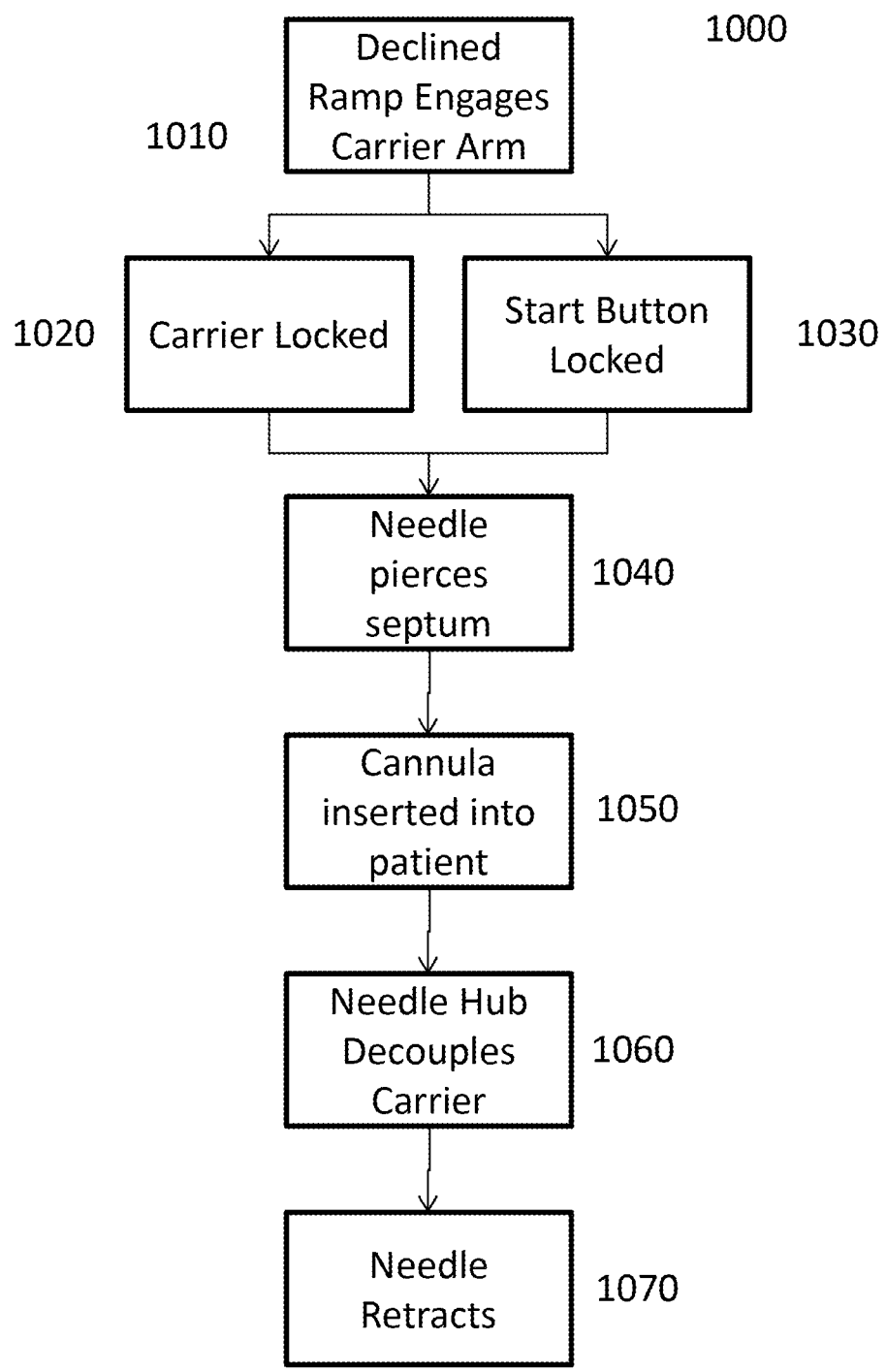
FIG. 10 is a flow diagram of the Carrier Insertion Process.

FIG. 9 graphically depicts the concurrent processes that are executed in response to a patient pressing the Start Button 105. In response to the Patient pressing (900) the Start Button, the Carrier Insertion Process 1000, Fluid Path Creation Process 1100 and the Pressurization System Activation Process are mechanically activated.

In the Carrier Insertion Process 1000, responsive to the patient pressing the Start Button 105, the Declined Ramp 310 engages the Carrier Arm 275. As the patient further presses the Start Button 105 to the locked position, the Carrier Arm 275 is forced by the Primary Spring 215 to disengage the Declined Ramp 310 and fall behind the Push Button 105 thereby locking the carrier 1020 and locking the Start Button 1030 in place. The locking force to hold the Carrier 220 and the Start Button 1030 is further augmented by force applied by the Start Spring 315. Subsequent to the Carrier Locking 1020 and the Start Button Locking 1030, the Needle 240A pierces (1040) the Exterior Septum 245. The Needle 240A and the Cannula 240B are then inserted (1040) into the patient 115 due to the stored potential energy released by the Primary Spring 215. The Release Tabs 250 of the Needle Hub Assembly 225 then decouple (1060) the Needle Hub Assembly 225 from the Carrier 220. The Needle Hub Assembly is then retracted (1070) due to the spring force exerted by the Secondary Spring 260.

Figure 11:
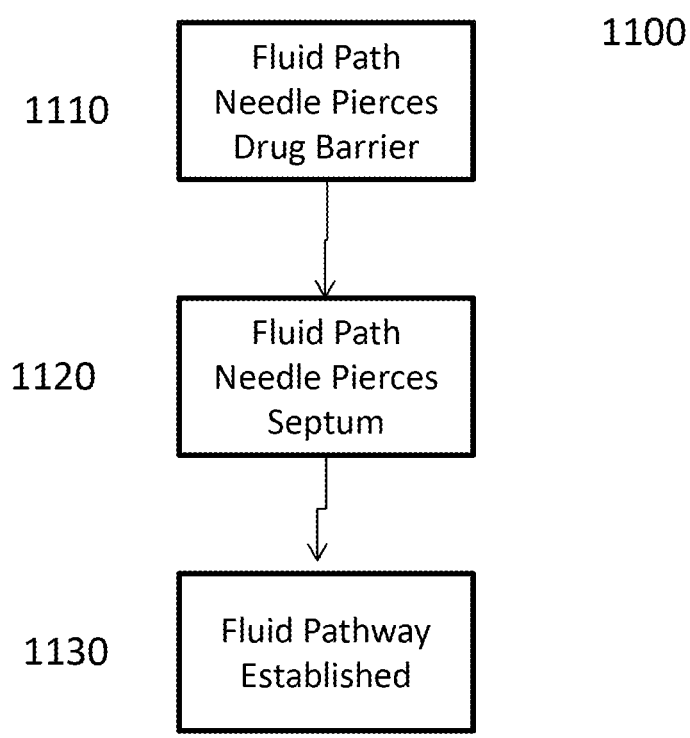
FIG. 11 is a flow diagram of the Fluid Path Creation Process.

FIG. 11 graphically depicts the Fluid Path Creation Process 1100 that is performed in response to the patient pressing (900) the Start Button 105. First the Fluid Path Needle 425 pierces (1110) the Drug Barrier 405. The Fluid Path Needle then pierces (1120) the Sterile Drug Barrier 405 and the Drug Container Septum 410. A fluid pathway is therefore established (1130) between the biologic and the patient 115.

Figure 12:
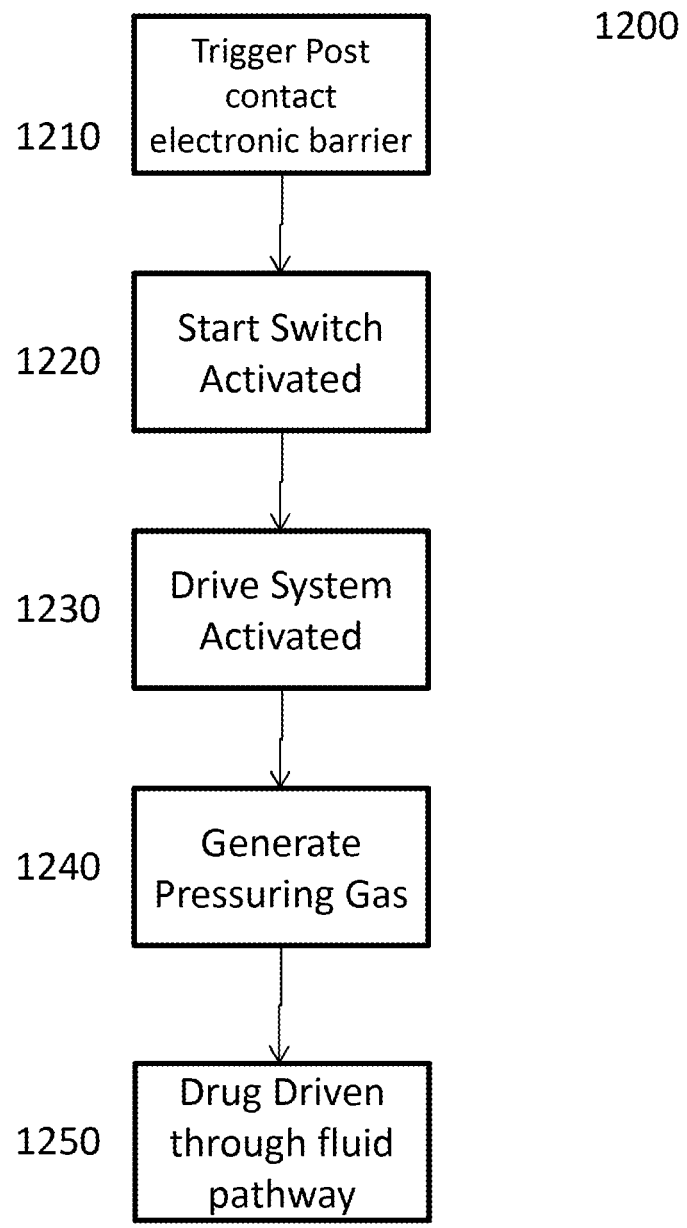
FIG. 12 is a flow diagram of Pressurization System Activation Process.

FIG. 12 graphically depicts the Pressurization System Activation Process 1200 that occurs in response to the patient pressing (900) the Start Button 105. First, the Triggering Post 620 contacts (1210) the Sterile Switching Barrier 625. The Trigger Post 620 then activates (1220) the Triggering Switch 630. Responsive to the Triggering Switch Activating 630, the Electronic Circuit Board 140 sends a signal to activate (1230) the Pressurization System 150. The signal may be a power signal that includes a variable voltage or a variable current. The signal may alternatively be a digital control signal. The Electronic Circuit Board 140 may provide the signal in order to obtain a desired flow rate of the biologic.

Responsive to receiving the signal, the Pressurization System 150 activates the one or more gas hydrogen generators 705. The one or more hydrogen generators 705 then generate (1240) the pressurizing gas. An amount of pressurizing gas produced may be produced in proportion to the received signal. For example, a particular provided current may correspond to a particular amount of gas generated. The pressurizing gas then drives (1250) the biologic from the container through the fluid delivery pathway into the patient 115.

Figure 13:
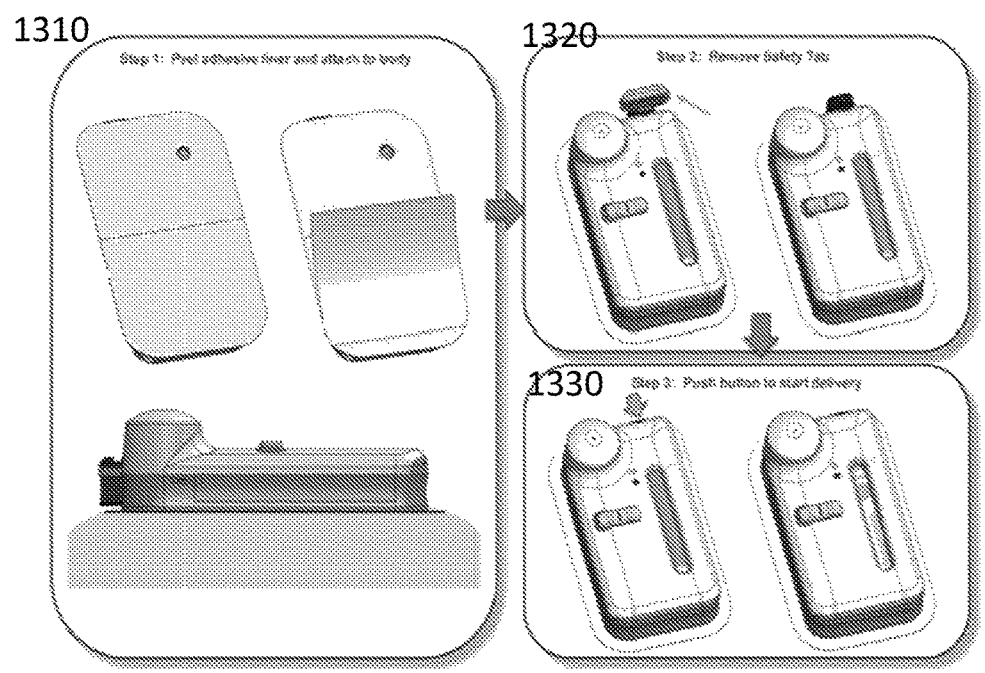
FIG. 13 is a flow diagram of the process of a user using the Patch Pump.

FIG. 13 graphically depicts the process of the patient 115 using the Patch Pump 100. First the patient removes (1310) an adhesive liner from the base 125. Then the patient removes (1320) the Removable Safety 170 from the Start Button 105. The patient then presses (1330) the Start Button 105 thereby causing the Carrier Insertion Process 1000, the Fluid Path Creation Process 1100, and the Pressurization System Activation Process 1200 to be activated.

Although features and elements are described above in particular combinations, one of ordinary skill in the art will appreciate that each feature or element can be used alone or in any combination with the other features and elements.

What is claimed is:

1. A device for subcutaneous drug delivery, the device comprising:
   a sterilized assembly; and
   a non-sterilized assembly that is mechanically coupled to sterilized assembly to form a combined assembly;
   wherein the sterilized assembly includes:
   a start button,
   a sterile drug barrier,
   a sterile electronic barrier, and
   a needle insertion mechanism mechanically coupled to the start button that comprises a carrier and primary spring;
   wherein the non-sterilized assembly includes:
   a pressurization system,
   a drug container that houses a sterile biologic, and electronic circuitry that includes a triggering switch;
wherein, responsive to being pressed by a patient, the start button:
punctures the sterile drug barrier with a fluid path needle integral to the start button,
punctures a septum of the drug container with the fluid path needle, and
establishes a fluid pathway;
wherein, responsive to being pressed by the patient, the start button further:
contacts the sterile electronic barrier with a triggering post integral to the start button, and
activates the triggering switch;
wherein, responsive to being pressed by the patient, the start button further:
moves a flat portion of the start button relative to a carrier arm to engage a declined ramp of the start button with the carrier arm, and
disengages the declined ramp to trigger the primary spring to release stored potential energy;
wherein, responsive to the triggering of the primary spring, the needle insertion mechanism:
moves the carrier and a needle hub assembly in a direction towards the patient, wherein the carrier and the needle hub assembly are coupled by release tabs,
inserts a cannula of the carrier into the patient,
uncouples the carrier and the needle hub assembly by forcing the release tabs to contact separators, and
fluidically connects the cannula to the fluid pathway;
wherein, responsive to the uncoupling of the carrier, the needle hub assembly:
releases the potential energy stored in a secondary spring, and
removes a needle from within the cannula by moving the needle hub assembly away from the patient;
wherein, responsive to the activation of the triggering switch, the electronic circuit:
supplies a signal to the pressurization system; and
wherein the pressurization system:
generates a pressurizing gas, in response to the signal, that forces the sterile biologic from the drug container through the fluid path and the cannula into the patient.

2. The device of claim 1, wherein the pressurization system contains one or more hydrogen generators;

wherein the one or more hydrogen generators generate the pressurizing gas in proportion to the signal supplied by the electronic circuit; and
wherein the electronic circuit:
determines the signal to obtain a desired flow rate of sterile biologic based upon a user flow control switch.

3. The device of claim 1, wherein the sterilized assembly further includes a drug viewing window; and
wherein the drug viewing window enables the patient to view the drug container.

4. The device of claim 1, wherein the sterilized assembly further includes a removable safety; and
wherein the removable safety is inserted into the start button and inhibits the patient from pressing the start button unless the removable safety is removed.

5. The device of claim 1, wherein the sterilized assembly further includes one or more visual indicators that display one or more indications of an operational status of the device.

6. The device of claim 1, wherein the sterilized assembly further includes a base that is in contact with the patient and is made of a material with a low thermal conductivity.

7. The device of claim 1, wherein the electronic circuit further includes a memory; and
wherein the memory stores information a time and a date when the patient administered the biologic.

8. The device of claim 1, wherein the non-sterilized assembly further includes a pressure sensor that monitors a pressure in the drug container; and
wherein the electronic circuit determines the signal based on the pressure sensor.

9. The device of claim 1, wherein, responsive to being pressed by the patient, the start button further:
locks the carrier in a position so that the cannula is held in position by a mechanical force in addition to a force provided by the primary spring; and
locks the start button so that it cannot be pressed again.

10. The device of claim 1, wherein the sterilized assembly further includes a base that is in contact with the patient and the base includes an adhesive liner that affixes the combined assembly to the patient.

* * * * *